United States Patent [19]
Cooley et al.

[11] Patent Number: 4,670,391
[45] Date of Patent: * Jun. 2, 1987

[54] SUNFLOWER REGENERATION THROUGH EMBRYOGENESIS AND ORGANOGENESIS

[75] Inventors: Gloria L. Cooley, Menlo Park; Anne S. Wilcox, Los Altos, both of Calif.

[73] Assignee: Sungene Technologies Corporation, Palo Alto, Calif.

[*] Notice: The portion of the term of this patent subsequent to Jun. 2, 2004 has been disclaimed.

[21] Appl. No.: 635,175

[22] Filed: Jul. 27, 1984

[51] Int. Cl.$^4$ .......................... C12N 5/00; C12N 5/02
[52] U.S. Cl. .................................. 435/240; 435/241; 800/1
[58] Field of Search ..................... 435/240, 241; 800/1

[56] References Cited

U.S. PATENT DOCUMENTS 4,354,327  10/1982  Smeltzer ................................. 47/58
4,552,844  11/1985  Everett ................................. 435/240

OTHER PUBLICATIONS

*The Yearbook of Agriculture,* 1961, U.S. Dept. Agriculture (plate).
Radford et al., 1968, *Manual of the Vascular Flora of the Carolinas,* U.N.C. Press, p. 1117.

*Primary Examiner*—Thomas G. Wiseman
*Assistant Examiner*—David T. Fox
*Attorney, Agent, or Firm*—Robbins & Laramie

[57] ABSTRACT

The present invention relates to the regeneration of sunflowers via embryogenesis and organogenesis. The process comprises the steps of:
(a) culturing tissue obtained from a sunflower plant on a first medium which comprises mineral salts, vitamins, amino acids, sucrose and a hormone in an amount sufficient to ensure callus formation;
(b) optionally subculturing said callus on a maintenance medium which comprises mineral salts, vitamins, amino acids, sucrose and a hormone in an amount sufficient for callus maintenance;
(c) subculturing said callus on a second medium which comprises mineral salts, vitamins, amino acids, sucrose and a hormone in an amount sufficient to precondition the callus;
(d) subculturing said callus on a third medium which comprises mineral salts, vitamins, sucrose and a hormone in an amount sufficient to ensure shoot formation, and
(e) subculturing said shoot on a fourth medium which comprises mineral salts, vitamins, sucrose and a hormone in an amount sufficient to ensure root formation, whereby plants are obtained.

32 Claims, No Drawings

SUNFLOWER REGENERATION THROUGH EMBRYOGENESIS AND ORGANOGENESIS

BACKGROUND OF THE INVENTION

1. Field of the Invention

The present invention relates to a process for the regeneration of sunflower plants from cell or tissue culture through embryogenesis and organogenesis. More specifically, cells or tissues of sunflower plants are cultured to produce calli. The calli can then be cultured for a prolonged period. The calli are then cultured on a preconditioning medium. The preconditioned calli are cultured to produce shoots which are cultured to produce roots whereby sunflower plants are produced. The present invention also relates to the sunflower plants and seeds which are produced by this method.

2. Description of the Prior Art

Several methods have been described in the prior art which result in the regeneration of sunflower. All of these methods have involved the use of organogenesis. However, these methods do not appear to be very efficient, and only result in the formation of a few regenerated plants. In organogenesis, plant parts are cultured on a first medium to induce callus formation. The callus can then be transferred to a second medium to induce shoot formation. The shoots are then transferred to a third medium to induce root formation, at which point the regenerated plantlets (plants) can be transferred to soil.

One example of inefficient organogenesis can be found in Sadu, *Indian J. Exp. Biol.*, pages 110-111 (June 1974). Sadu reported the regeneration of sunflower by culturing stem pith tissue to form a callus which differentiated to form plantlets. The medium was the same throughout the regeneration scheme.

The medium used to form the callus and to differentiate into plants was a modified White's medium containing 1 ppm of the hormone indole acetic acid (IAA). The modified White's medium contained the following ingredients in one liter of medium:

| Component | Weight (mg) | Component | Weight (mg) |
|---|---|---|---|
| $NH_4NO_3$ | 400 | $ZnSO_4$ | 2.7 |
| KCl | 65 | thiamine | 0.2 |
| $KNO_3$ | 80 | nicotinic acid | 0.5 |
| $KH_2PO_4$ | 12.5 | pyridoxine | 0.5 |
| $Ca(NO_3)_2.H_2O$ | 144 | glycine | 2.0 |
| $MgSO_4.7H_2O$ | 7.2 | inositol | 100 |
| $Na_2$ EDTA | 25 | sucrose | 20000 |
| $H_3BO_3$ | 1.6 | agar | 6000 |
| $MnSO_4.4H_2O$ | 6.5 | | |

It was found that 2,4-dichlorophenoxyacetic acid (2,4-D) promoted callus growth but did not support differentiation of the callus. The addition of 0.1 ppm kinetin resulted in callus growth but no differentiation.

Chandler and Jan describe the regneration of sunflower from immature embryos of interspecific crosses. The immature embryos are grown on growth medium as described by Chandler and Beard, below. After 2 to 3 weeks, the enlarged embryos are transferred to tubes containing MS medium (MS mineral salts, vitamins and sucrose) containing IAA and kinetin, generally used at 0.3 ppm and 1.0 ppm, respectively. The tubes are cultured at 28° C. in the light to produce calli which then form shoots. Shoots are usually transferred to a MS medium containing no hormones but containing 0.2% activated charcoal to cause root formation. The plantlets are then transferred to soil.

Heaton discloses the regeneration of the domestic sunflower *Helianthus annus* L. from immature embryos. The immature embryos were plated on Gibco Murashige Shoot-Tip Rooting Medium. Callus formation was induced using 3% sucrose, 0.3 mg/l IAA and 1.0 mg/l kinetin. The embryos were kept in the dark for two weeks, then in the light for 12 hours per day. After five weeks, shoots formed on the callus. The shoots were transferred to rooting medium for plantlet production.

Binding et al, *Z. Pflanazenphysiol.* 101, 119 (1981) describe the regeneration of shoots of the sunflower *Helianthus annus* from protoplasts. Protoplasts were cultured in V-KM medium to form callus, and the calli were transferred to a low osmotic medium. The low osmotic medium comprises B5 medium with 15 $\mu$M 6-benzylaminopurine (BA). Shoots formed on this medium.

Rogers et al, *In Vitro* 9, 463 (1974) describe the production of roots from a callus in *Helianthus annus*. This was performed by culturing plant tissue sequentially on three media. The first medium comprises MS basal medium with 1 mg/l $\alpha$-naphthalene acetic acid (NAA), 1 mg/l kinetin and 5 mg/l 2,4-D. The second medium comprises MS basal medium with 0.5 mg/l kinetin and 2 mg/l IAA. The third medium comprises 0.05 mg./l kinetin and 0.1 mg/l IAA. No whole plants were produced by this method.

One additional method has been described to produce sunflower plants from an embryo. This method has found use in producing plants from embryos which do not develop in the original plant itself, either because of embryo abortion or seed dormancy resulting from the hybridization of non-compatible species. This method is embryo culture, and has been described by Chandler and Beard in *The Sunflower*, pages 45-47 (August/September 1980) and *Crop Science* 23, 1004 (1983). This process involves the rescue of the embryo prior to abortion followed by maturation of the embryo and germination to form the plant.

In this process, young embryos were isolated 3 to 7 days after pollination. These embryos were usually less than 0.1 mm in diameter. The embryos were plated on a solid, growth medium which contained B5 salts, vitamins, amino acids, the auxin $\alpha$-naphthalene acetic acid (NAA) at a concentration of 0.05 mg/l, and 12% sucrose. It was found that if 9% sucrose was utilized instead of 12% and 1.0 mg/l indoleacetic acid (IAA) was used instead of NAA, then the young embryos has a tendency to grow as undifferentiated callus instead of embryos. In addition, very young embryos also germinated prematurely on this latter medium.

After 1 to 2 weeks, the enlarged (2-6 mm in diameter) embryos were transferred to a liquid medium for germination of the embryos to plants. During the enlargement period, some of the embryos began root formation and pigment synthesis. The embryos were matured to the cotyledon stage in order to obtain plant formation. The liquid, germination medium contained B5 salts and 1% sucrose. After the embryo generated roots and a shoot, it was transplanted to soil.

The present invention is the first instance of a general method for obtaining sunflower plants, i.e., regenerating sunflowers, through the use of embryogenesis and organogenesis. Sunflower plants and seeds are produced by this process. The sunflower plants resulting from this process may differ from the starting plant material as a result of somoclonal variation. The pathway is also useful in that it will enable the use of various selection processes to provide further variation. The plants which are produced can then be used in conventional breeding programs.

SUMMARY OF THE INVENTION

The present invention is directed to a process for regenerating sunflowers, particularly to regenerating cultivars of domestic sunflower, *Helianthus annus*. This process uses embryogenesis and organogenesis. The process comprises the steps of inducing callus formation on an induction medium from tissue of a sunflower plant, maintaining the calli, culturing the calli on a preconditioning medium, forming shoots on a shoot forming medium and forming roots on a root forming medium.

More specifically, the present process comprises the steps of:
(a) culturing tissue obtained from a sunflower plant on a first medium which comprises mineral salts, vitamins, amino acids, sucrose and a hormone in an amount sufficient to ensure embryogenic callus formation;
(b) optionally subculturing said callus on a maintenance medium which comprises mineral salts, vitamins, amino acids, sucrose and a hormone in an amount sufficient for embryogenic callus maintenance,
(c) subculturing the calli on a second medium which comprises mineral salts, vitamins, amino acids, sucrose and a hormone in an amount sufficient to precondition said callus.
(d) subculturing said calli on a third medium which comprises mineral salts, vitamins, sucrose and a hormone in an amount sufficient to ensure shoot formation, and
(e) subculturing said shoot on a fourth medium which comprises mineral salts, vitamins, sucrose, and a hormone in an amount sufficient to ensure root formation, whereby plants are obtained.

The source of tissue is preferably immature embryos from the HA 300, RHA 271, and HA 89 cultivars of *Helianthus annus*. The first, maintenance and second media preferably contain modified B5 mineral salts, the vitamins and amino acids as described by Chandler and Beard, supra. The third medium preferably contains MS mineral salts and vitamins, described by Henderson et al, *Am.J.Botany* 39, 467 (1952) which have been modified. The fourth medium preferably contains MS mineral salts.

The preferred hormones are 2,4-D and abscisic acid (ABA) in the first medium, ABA in the maintenance medium, BA or ABA and BA in the second medium, IAA and kinetin in the third medium, and IAA in the fourth medium.

DETAILED DESCRIPTION OF THE INVENTION

The present invention is directed to a process for regenerating sunflowers, especially the domestic sunflower *Helianthus annus*, via embryogenesis and organogenesis. In this process, embryogenic callus is formed which is preconditioned so that shoots are first obtained from tissue culture and then roots. The plants are then placed in soil for growth to maturation. The present invention is also directed to sunflower plants obtained by this process and to seeds from these plants.

In general, the process comprises (a) culturing tissue obtained from a sunflower plant on a first medium to produce embryogenic calli, (b) optionally culturing the calli on a maintenance medium to maintain the embryogenic calli, (c) culturing the calli on a second medium to precondition the calli, (d) culturing the preconditioned calli on a third medium to produce shoots, and (e) culturing the shoots on a fourth medium to produce roots. After plantlets have been developed, they can be grown in soil.

The plant tissue which is preferred for use in the initiation of callus is the immature embryo. The immature embryos with pericarps are isolated from the sunflower heads when the embryos are in the range of 0.5 to 2.0 mm. The embryos are sterilized with bleach and rinsed with sterile water. The immature embryos are isolated from the pericarps and plated onto an embryogenic callus induction medium, hereinafter referred to as the first medium.

The medium comprises mineral salts, vitamins, amino acids, sucrose and a hormone in an amount sufficient for callus formation. The mineral salts comprise macroelements and microelements. The macroelements used in the first medium may be the following compounds: magnesium sulfate, calcium chloride, monosodium phosphate, potassium nitrate and ammonium sulfate. The microelements contained in this medium are: boric acid, manganese sulfate, zinc sulfate, sodium molybdate (VI), copper (II) sulfate, cobalt chloride, potassium iodide, iron (II) sulfate and disodium ethylenediaminetetraacetic acid (EDTA). This combination of mineral salts is known in the art as the B5 mineral salts. In the first medium, the B5 mineral salts have been modified so that the medium contains less iron and EDTA than the standard B5 mineral salts. It is also preferred to use less copper and iodine.

In this medium, the iron is chelated by the EDTA. Citric acid can be utilized in place of the EDTA as the chelating agent. In a preferred embodiment, chelated iron is added in preparing the medium rather than adding iron (II) sulfate and disodium-EDTA.

The preferred amounts of the macroelements and microelements which are used to prepare one liter of medium are as follows: 250 mg magnesium sulfate heptahydrate, 150 mg calcium chloride dihydrate, 150 mg monosodium phosphate monohydrate, 2500 mg potassium nitrate, 134 mg ammonium sulfate, 3 mg boric acid, 10 mg manganese sulfate monohydrate, 2 mg zinc sulfate heptahydrate, 0.25 mg sodium molybdate (VI) dihydrate, 0.0025 mg copper (II) sulfate pentahydrate, 0.025 mg cobalt chloride hexahydrate, 0.075 mg potassium iodide, 2.78 mg iron (II) sulfate heptahydrate, and 3.73 mg disodium-EDTA.

In a more preferred embodiment, the iron concentration is 0.20–3.25 mg/l, preferably 0.81 mg/l. This may be added to the medium in any of the forms described above.

The first medium also contains vitamins. The vitamins which are utilized include nicotinic acid, thiamine, pyridoxine and myo-inositol. The vitamins have been described by Chandler and Beard, supra. The preferred amounts of vitamins needed to prepare one liter of medium are: 1 mg nicotinic acid, 10 mg thiamine hydrochloride, 1 mg pyridoxine hydrochloride and 4000 mg myo-inositol. This combination of vitamins will be referred to as the Chandler vitamins.

The first medium further contains amino acids. The amino acids are: alanine, glutamine, serine, tryptophan and cysteine. All amino acids are in the L-form unless otherwise indicated. The amino acids have been described by Chandler and Beard, supra. The preferred amounts of amino acids used to prepare one liter of medium are: 1000 mg alanine, 800 mg glutamine, 160 mg serine, 50 mg tryptophan, and 10 mg cysteine. This combination of amino acids will be referred to as the Chandler amino acids.

The first medium also contains sucrose and a hormone. The sucrose is utilized in the amount of 7%–14%, with 12% being preferred. The hormone which may be utilized is a mixture of ABA and 2,4-D, 1.0–7.0 $\mu$M ABA and 5.0–12.0 $\mu$M 2,4-D are utilized. Preferably, 5 $\mu$M ABA and 10 $\mu$M 2,4-D are used. Agar is used to solidify the medium. A final concentration of 0.7% has been found to be satisfactory. The medium has a pH of 5.5–6.0, with a preferred pH of 5.8.

The medium is sterilized by autoclaving all components except the vitamins and amino acids which are sterilized via microporous membrane filtration.

The immature embryos are plated on the first medium and cultured in the dark for about 7 to 14 days. It is preferred to use 7 to 10 days of culturing. During this time, the embryo undergoes dedifferentiation and callus formation.

After culturing the embryos on the first medium, the callus which is formed may optionally be transferred and subcultured on a maintenance medium before transfer to the second medium. When this step is performed, the callus is subcultured on this medium for about 2 weeks in the dark. The callus can be subcultured on this medium for a prolonged period with transfer occurring at approximately 2 week intervals.

The maintenance medium comprises mineral salts, vitamins, amino acids, sucrose and a hormone in an amount sufficient to maintain embryogenic callus. The mineral salts comprise macroelements and microelements. The macroelements and microelements are as described for the first medium. The vitamins and amino acids are as described for the first medium. The sucrose concentration is 7%–14%, with 12% being preferred. The hormone is preferably ABA, and is used in an amount of 0.05–1.0 $\mu$M. It is preferred to use 1 $\mu$M ABA. Agar is added to the medium to solidify it. A concentration of 0.7% is satisfactory. The medium has a pH of 5.5–6.0, with 5.8 preferred. The medium is sterilized as described above.

After culturing the callus on the maintenance medium for 2 weeks, or desired intervals thereof, the callus is transferred and subcultured on a preconditioning medium, hereinafter referred to as the second medium. The callus is subcultured on this medium for 1 to 2 weeks, preferably 1 week, in the dark. If the callus from the first medium is not cultured on the maintenance medium, it is transferred directly to the second medium.

The second medium comprises mineral salts, vitamins, amino acids, sucrose and a hormone in an amount to precondition the callus. The mineral salts, vitamins and amino acids are as described for the first medium. The sucrose concentration is 4%–8%, with 6% being preferred. The hormone is preferably BA or a mixture of ABA and BA in an amount of 0.5–2.0 $\mu$M BA or a mixture of 1.0–4.0 $\mu$M ABA and 0.5–2.0 $\mu$M BA. It is preferred to use 3 $\mu$M ABA and 1 $\mu$M BA. Agar is added to the medium to solidify it. 0.7% has been found to be satisfactory. The medium has a pH of 5.5–6.0, with 5.8 preferred. The medium is sterilized as described above.

After culturing the callus on the second medium, the callus is transferred and subcultured on a shoot formation medium, hereinafter referred to as the third medium. The callus is subcultured on the third medium for 2 to 4 weeks in the light, with a photoperiod of 12 to 16 hours per day, preferably 16 hours per day. During this time, shoots are formed on the callus.

The third medium comprises mineral salts, vitamins, sucrose and IAA in an amount sufficient for shoot formation. The mineral salts comprise macroelements and microelements. The macroelements which are utilized in the fourth medium are: magnesium sulfate, calcium chloride, monopotassium phosphate, potassium nitrate and ammonium nitrate. The microelements contained in this medium are: boric acid, manganese sulfate, zinc sulfate, sodium molybdate (VI), copper (II) sulfate, cobalt chloride, potassium iodide, iron (II) sulfate and disodium-EDTA. This combination of mineral salts is known in the art as the MS mineral salts.

The preferred amounts of the macroelements and microelements which are used to prepare one liter of medium are: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 27.8 mg iron (II) sulfate heptahydrate, and 37.3 mg disodium-EDTA.

The third medium further contains vitamins. The vitamins which are present in this medium include thiamine, pyridoxine, myo-inositol, riboflavin, pantothenate, p-aminobenzoic acid, niacin, choline, folic acid and biotin. These vitamins have been described by Henderson et al, supra. The preferred amounts of the vitamins used to prepare one liter of medium are: 0.5 mg thiamine hydrochloride, 0.1 mg pyridoxine hydrochloride, 100.5 mg myo-inositol, 0.05 mg riboflavin, 0.8 mg calcium pantothenate, 0.05 mg p-aminobenzoic acid, 0.5 mg niacin, 0.1 mg choline hydrochloride, 0.1 mg folic acid, and 0.005 mg biotin. This combination of vitamins will be referred to as the Henderson vitamins which have been modified to contain 100 mg/l more myo-inositol and 0.4 mg/l more thiamine hydrochloride.

The third medium also contains sucrose and a hormone, which is preferably a mixture of IAA and kinetin. The sucrose is utilized in the amount of 2%–4%, with 3% being preferred. The IAA is utilized in an amount of 0.3–3.0 $\mu$M IAA and 0.5–9.0 $\mu$M kinetin. It is preferred to use 0.3 $\mu$M IAA and 5 $\mu$M kinetin. Agar is added to the medium to solidify it. A concentration of 0.7% is satisfactory for this purpose. The medium has a pH 5.5–6.0, with 5.8 preferred. The medium is sterilized as described above.

The shoots are transferred from the third medium to the fourth medium, when they are 2 cm long. If the shoots have not elongated properly or if the shoots begin in vitro flowering, they may be transferred to fresh third medium or to the third medium having either (a) IAA in an amount described above and reduced kinetin (generally, 0.5–4.5 $\mu$M with 2.0 $\mu$M preferred), or (b) 15–25 $\mu$M adenine sulfate and containing no IAA. The shoots are subcultured on a solid, root formation medium, hereinafter referred to as the fourth medium. The shoots are subcultured on this medium for 6 to 10 days in the light, with a photoperiod of 12–16 hours per day, preferably 16 hours per day.

The fourth medium comprises mineral salts, vitamins, sucrose and a hormone. The mineral salts comprise macroelements and microelements. The macroelements and microelements are as described for the third medium. The vitamins are myo-inositol and thiamine. Preferably, these are present in the amounts of 100 mg/l of myo-inositol and 0.4 mg/l of thiamine hydrochloride. The sucrose concentration is 2%–3%, with 2% being preferred. Agar is added to solidify the medium. A concentration of 0.7% is satisfactory for this purpose. The hormone is preferably IAA and is used in an amount of 0.05–0.5 $\mu$M, with 0.1 $\mu$M being preferred. The fourth medium is sterilized by autoclaving, and has a pH of 5.5–6.0, with a preferred pH of 5.8.

After 5 to 14 days on the fourth medium, the plantlets can be transferred to soil and the greenhouse. This is generally accomplished by transferring the plantlets to soil which is well moistened and contained in a high humidity chamber. Once the plantlets are established, they are removed from the high humidity chamber, transplanted to soil, and grown to maturity. Seeds are produced by the mature plants.

The above process is useful for regenerating plantlets from tissue of many cultivars of domestic sunflower. The process is especially useful for regenerating plantlets from *Helianthus annus* cv. HA 89, HA 300 and RHA 271.

The present invention will be further described by reference to the following non-limiting examples. When the materials are cultured in the light, it is understood to mean light having a photoperiod of 16 hours per day and at a temperature of 25°–29° C. unless indicated otherwise.

EXAMPLE 1

Preparation of Stock Solutions

1. Mineral Salts

A. Modified B5

A 10X modified B5 mineral salts stock solution was prepared by dissolving the following ingredients in 1000 ml of distilled, deionized water.

| Component | Weight (mg) | Component | Weight (mg) |
| --- | --- | --- | --- |
| MgSO$_4$.7H$_2$O | 2500 | ZnSO$_4$.7H$_2$O | 20 |
| CaCl$_2$.2H$_2$O | 1500 | Na$_2$MoO$_4$.2H$_2$O | 2.5 |
| NaH$_2$PO$_4$.H$_2$O | 1500 | CuSO$_4$.5H$_2$O | 0.025 |
| KNO$_3$ | 25000 | CoCl$_2$.6H$_2$O | 0.25 |
| (NH$_4$)$_2$SO$_4$ | 1340 | KI | 0.75 |
| H$_3$BO$_3$ | 30 | FeSO$_4$.7H$_2$O | 27.8 |
| MnSO$_4$.H$_2$O | 100 | Na$_2$ EDTA | 37.3 |

The stock solution was divided into 100 ml aliquots.

2. Vitamins and Amino Acids

A. Chandler Vitamins and Amino Acids

A 40X stock solution of Chandler vitamins and amino acids was prepared. The stock solution was made by dissolving the following components in 500 ml of distilled, deionized water.

| Component | Weight (g) | Component | Weight (g) |
| --- | --- | --- | --- |
| nicotinic acid | 0.02 | glutamine | 16 |
| thiamine.HCl | 0.2 | serine | 3.2 |
| pyridoxine.HCl | 0.02 | tryptophan | 1.0 |
| myo-inositol | 80 | cysteine | 0.2 |
| alanine | 20 | | |

This solution was sterilized by membrane filtration using an 0.2$\mu$ Gelman filter prior to addition to the media.

B. Henderson Vitamins

A 1000X stock solution of Henderson vitamins (unmodified) was prepared by dissolving the following components in 200 ml of distilled, deionized water.

| Component | Weight (mg) | Component | Weight (mg) |
| --- | --- | --- | --- |
| thiamine.HCl | 20 | p-amino-benzoic acid | 10 |
| pyridoxine.HCl | 20 | niacin | 100 |
| myo-inositol | 100 | choline.HCl | 20 |
| riboflavin | 10 | folic acid | 20 |
| Ca pantothenate | 160 | biotin | 1 |

This solution was sterilized by membrane filtration prior to use as described above.

3. Hormones

A. A 1 mM stock solution of 2,4-D was prepared by dissolving 0.1105 g of 2,4-D in a couple ml of 1M KOH and diluting to 500 ml with distilled, deionized water.

B. A 2 mM stock solution of IAA was prepared by dissolving 0.0876 g of IAA in a couple ml of 1M KOH and diluting to 250 ml with distilled, deionized water.

C. A 1 mM stock solution of kinetin was prepared by dissolving 0.108 g of kinetin in a couple ml of 1M HCl and diluting to 500 ml with distilled, deionized water.

D. A 1 mM stock solution of ABA was prepared by dissolving 0.132 g of ABA in a couple ml of 1M KOH and diluting to 500 ml with distilled, deionized water.

E. A 1 mM stock solution of BA was prepared by dissolving 0.113 g of BA in a couple ml of 1M HCl and diluting to 500 ml with distilled, deionized water.

F. A 1 mg/ml stock solution of adenine sulfate was prepared by dissolving 100 mg of adenine sulfate in 100 ml of distilled, deionized water.

EXAMPLE 2

A. First Medium or Callus Induction Medium

The first medium was prepared by adding 10 ml of the 2,4-D stock solution, 5 ml of the ABA stock solution, 120 g of sucrose and 7 g of agar to 100 ml of the modified B5 stock solution, and the volume brought to 975 ml with distilled, deionized water. The pH was adjusted to 5.8 with 1M KOH and the mixture autoclaved at 120 psi for 15 minutes. 25 ml of the Chandler vitamins and amino acids stock solution, which had been sterilized as described above, was added to the cooling medium which was then poured into petri dishes.

To prepare first medium with different concentrations of 2,4-D and ABA, the appropriate amount of the 2,4-D and ABA stock solutions were used. For example, to prepare a first medium having 5 $\mu$M 2,4-D and 1 $\mu$M ABA instead of 10 $\mu$M 2,4-D, and 5 $\mu$M ABA 5 ml of the 2,4-D stock solution and 1 ml of the ABA stock solution were used.

B. Callus Maintenance Medium

The maintenance medium was prepared by adding 1 ml of the ABA stock solution, 120 g of sucrose and 7 g of agar to 100 ml of the modified B5 stock solution, and the volume brought to 975 ml with distilled, deionized water. The pH was adjusted to 5.8 with 1M KOH and the mixture autoclaved at 120 psi for 15 minutes. 25 ml of the Chandler vitamins and amino acids stock solution, sterilized by membrane filtration as described above, was added to the cooling medium which was then poured into petri dishes.

To prepare maintenance medium having a different concentration of ABA, the appropriate amount of the ABA stock solution was used in the manner described above.

C. Second Medium or Callus Preconditioning Medium

The second medium was prepared by adding 3 ml of the ABA stock solution, 1 ml of the BA stock solution, 60 g of sucrose and 7 g of agar to 100 ml of the modified B5 stock solution, and the volume brough to 975 ml with distilled, deionized water. The pH was adjusted to 5.8 with 1M KOH and the mixture autoclaved at 120 psi for 15 minutes. 25 ml of the Chandler vitamins and amino acids stock solution, sterilized by the membrane filtration as described above, was added to the cooling medium which was then poured into petri dishes.

To prepare second medium having different concentrations of ABA and BA, the appropriate amounts of the ABA and BA stock solutions were used in the manner as described above.

D. Third Medium or Shoot Formation Medium

The third medium was prepared by dissolving one packet of powdered Murashige minimal organics medium without sucrose (obtained from Gibco Laboratories and which contains the MS mineral salts, 100 mg myo-inositol and 0.4 mg thiamine hydrochloride), 30 g of sucrose and 7 g of agar in 500 ml of distilled, deionized water. 0.05 ml of the IAA stock solution and 5 ml of the kinetin stock solution were then added, and the volume brought to 999 ml with distilled, deionized water. The pH was adjusted to 5.8 with 1M KOH and the mixture autoclaved at 120 psi for 15 minutes. 1 ml of the Henderson vitamins stock solution, sterilized as described above, was added to the cooling medium. The mixture was then poured into petri dishes.

The procedure described above was utilized to prepare third medium having different IAA and kinetin concentrations.

To prepare the third medium containing adenine sulfate instead of IAA and kinetin, the desired amount of the adenine sulfate stock solution was added in place of the IAA and kinetin stock solutions. For example, to prepare this medium having 22 $\mu$M adenine sulfate, 4 ml of the adenine sulfate stock solution was added.

E. Fourth Medium or Root Formation Medium

The fourth medium was prepared by dissolving one packet of powdered Murashige minimal organics medium without sucrose, 20 g of sucrose and 7 g of agar in 1000 ml of distilled, deionized water. 0.05 ml of the IAA stock solution was then added. The pH was adjusted to 5.8 with 1M KOH. The mixture was autoclaved at 120 psi for 15 minutes. The cooling medium was poured into petri dishes.

To prepare the fourth medium having a different IAA concentration, the appropriate amount of the stock solution was added as described above.

EXAMPLE 3

Sunflower Regeneration

Immature embryos with pericarps were isolated from the head of the sunflower *Helianthus annus* cv. RHA 271 when they were 0.5 to 2 mm in size. RHA 271 was obtained from Sigco Research, Incorporated. The emryos with pericarps were sterilized with a 20% bleach solution for 10 minutes. They were then rinsed with sterile water. The immature embryos were separated from the pericarps, endosperm and embryo sac and plated onto the first medium, contained in a petri dish. The first medium was prepared as described in the preceding example, using 10 $\mu$M 2,4-D and 5 $\mu$M ABA. The petri dish was placed in the dark and cultured for 10 days to form calli.

At this time, each callus was transferred to the maintenance medium, which was prepared as described above, using 1 $\mu$M ABA, and also contained in a petri dish. The callus was cultured on this medium for 10 days in the dark.

Each callus was then transferred to the second medium. The third medium was prepared as described in Example 2, using 3 $\mu$M ABA and 1 $\mu$M BA. The callus was cultured on this medium for 10 days in the dark.

At this time, each callus was transferred to the third medium, which was prepared as described above, using 0.3 $\mu$M IAA and 5 $\mu$M kinetin, and also contained in a petri dish. The callus was cultured on this medium for 14 days in the light. The callus differentiated to form shoots.

The shoots 2 cm long were then transferred to the fourth medium, also contained in petri dishes. The fourth medium was prepared as described above, using 0.1 $\mu$M IAA. The shoots were cultured on this medium for 9 days in the light. During this time period, the shoots formed roots. The shoots which were not 2 cm long or which had begun in vitro flowering were transferred to fresh third medium containing 0.3 $\mu$M IAA and 2 $\mu$M kinetin, and cultured in the light for 8 days before being transferred to the fourth medium.

After 9 days, the plantlets were transferred to soil in the greenhouse. The plantlets were planted in cubes, and the soil was well moistened. The cubes were placed in a sweater box and covered with a second sweater box to maintain a high humidity environment. The soil was kept well moistened for 5 days, after which the plantlets were transferred to 12 inch pots. The pots were watered three times weekly and fertilized every 10 days. The plants were hand-pollinated, and maintained until the seeds were mature. Seeds were then harvested and stored for future use. Some seeds from one of the regenerants were planted and germinated to produce sunflower plants.

EXAMPLES 4–18

The above procedure was essentially followed with some variation in the culture periods using different cultivars and different hromone concentrations. *Helianthus annus* cv. HA 89 and HA 300 were obtained from Sigco Research, Incorporated.

| | | HORMONE CONCENTRATION (μM) | | | | | | |
|---|---|---|---|---|---|---|---|---|
| | | First Medium | | Maint. Medium | Second Medium | | Third Medium | | Fourth Medium |
| Example | Cultivar | 2,4-D | ABA | ABA | ABA | BA | IAA | Kinetin | IAA |
| 4 | RHA 271 | 12 | 1 | 0.5 | 4 | 0.5 | 3.0 | 0.5 | 0.5 |
| 5 | HA 89 | 10 | 4 | 1.0 | 3 | 1.5 | 1 | 7.0 | 0.1 |
| 6 | HA 89 | 5 | 7 | 0.75 | 4 | 0.5 | 0.3 | 5 | 0.05 |
| 7 | RHA 271 | 8 | 8 | 0.05 | 1 | 2 | 0.3 | 9 | 0.05 |
| 8 | HA 89 | 10 | 2 | 0.5 | 3 | 1 | 0.5 | 9 | 0.5 |
| 9 | HA 89 | 10 | 5 | — | 2 | 2 | 2 | 4 | 0.1 |
| 10 | HA 300 | 5 | 7 | 1.0 | 2 | 1 | 0.3 | 5 | 0.1 |
| 11 | HA 300 | 10 | 4 | 0.5 | 3 | 1 | 3 | 0.5 | 0.3 |
| 12 | RHA 271 | 5 | 7 | 1 | 3 | 1 | 2 | 2 | 0.4 |
| 13 | HA 89 | 10 | 5 | 0.1 | 3 | 0.5 | 1 | 3 | 0.1 |
| 14 | HA 89 | 12 | 1 | 1.0 | 2 | 1.5 | 0.3 | 5 | 0.2 |
| 15 | HA 300 | 10 | 5 | 1.0 | 1 | 2 | 2 | 7 | 0.1 |
| 16 | RHA 271 | 10 | 5 | — | 2 | 2 | 0.3 | 5 | 0.3 |
| 17 | HA 89 | 5 | 5 | 1.0 | 3 | 1 | 0.3 | 5 | 0.5 |
| 18 | RHA 271 | 10 | 4 | 1.0 | — | 1 | 0.5 | 6 | 0.1 |

Some seeds from some of the HA 89 regenerants were planted and germinated to produce sunflower plants.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating sunflower plants from cell or tissue culture through embryogenesis and organogenesis which comprises the steps of:
   (a) culturing tissue obtained from a sunflower plant on a first medium which comprises mineral salts, vitamins, amino acids, sucrose and a mixture of abscisic acid (ABA) and 2,4-dichlorophenoxyacetic acid (2,4-D) in an amount sufficient to ensure callus formation;
   (b) subculturing said callus on a second medium which comprises mineral salts, vitamins, amino acids, sucrose and 6-benzylaminopurine (BA) or a mixture of ABA and BA in an amount sufficient to ensure callus preconditioning;
   (c) subculturing said preconditioned callus on a third medium which comprises mineral salts, vitamins, sucrose and a mixture of indoleacetic acid (IAA) and kinetin in an amount sufficient to ensure shoot formation, and
   (d) subculturing said shoot on a fourth medium which comprises mineral salts, vitamins, sucrose and IAA in an amount sufficient to ensure root formation, whereby plants are obtained.

2. The process of claim 1 wherein said tissue is immature embryos.

3. The process of claim 1 wherein said callus is subcultured on a maintenance medium which comprises mineral salts, vitamins, amino acids, sucrose and ABA in an amount sufficient to ensure callus maintenance prior to subculturing on said second medium.

4. The process of claim 3 wherein the concentrations of ABA, 2,4-D, IAA, BA and kinetin are:
   (1) 5.0–12.0 μM 2,4-D and 1.0–7.0 μM ABA in said first medium;
   (2) 0.05–1.0 μM ABA in said maintenance medium;
   (3) 0.5–2.0 μM BA or 1.0–4.0 μM ABA and 0.5–2.0 μM BA in said second medium;
   (4) 0.3–3.0 μM IAA and 0.5–9.0 μM kinetin in said third medium, and
   (5) 0.05–0.5 μM IAA in said fourth medium.

5. The process of claim 4 wherein the concentration of sucrose is:
   (1) 7%–14% in said first medium;
   (2) 7%–14% in said maintenance medium;
   (3) 4%–8% in said second medium;
   (4) 2%–4% in said third medium, and
   (5) 2%–3% in said fourth medium.

6. The process of claim 5 wherein said mineral salts of said first, maintenance and second media comprise magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron.

7. The process of claim 6 wherein said mineral salts are the B5 mineral salts modified so that the concentration of the copper sulfate is 0.0025 mg/l and the concentration of the potassium iodide is 0.075 mg/l and the chelated iron contains 0.81 mg/l iron.

8. The process of claim 5 wherein said vitamins of said first, maintenance and second media comprise nicotinic acid, thiamine, pyridoxine and myo-inositol.

9. The process of claim 8 wherein said vitamins are the Chandler vitamins.

10. The process of claim 5 wherein said amino acids of said first, maintenance and second media are alanine, glutamine, serine, tryptophan and cysteine.

11. The process of claim 10 wherein said amino acids are the Chandler amino acids.

12. The process of claim 5 wherein said mineral salts of said third and fourth medium comprise magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA.

13. The process of claim 12 wherein said mineral salts are the MS mineral salts.

14. The process of claim 5 wherein said vitamins of said third medium are thiamine, pyridoxine, myo-inositol, riboflavin, calcium pantothenate, p-aminobenzoic acid, niacin, choline and folic acid.

15. The process of claim 14 wherein said vitamins are the Henderson vitamins, modified to contain 100.5 mg/l myo-inositol and 0.5 mg/l thiamine hydrochloride.

16. The process of claim 5 wherein said vitamins of said fourth medium are myo-inositol and thiamine.

17. A process for regenerating sunflower plants from cell or tissue culture through embryogenesis and organogenesis which comprises the steps of:
(a) culturing tissue obtained from a sunflower plant on a first medium which comprises mineral salts consisting of magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron, vitamins consisting of nicotinic acid, thiamine, pyridoxine and myo-inositol, amino acids consisting of alanine, glutamine, serine, tryptophan and cysteine, sucrose and a mixture of 2,4-dichloropehnoxyacetic acid (2,4-D) and abscisic acid (ABA) in an amount sufficient to ensure callus formation;
(b) subculturing said callus on a second medium which comprises mineral salts consisting of magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron, vitamins consisting of nicotinic acid, thiamine, pyridoxine and myo-inositol, amino acids consisting of alanine, glutamine, serine, tryptophan and cysteine, sucrose and 6-benzylaminopurine (BA) or a mixture of ABA and BA in an amount sufficient to ensure callus preconditioning;
(c) subculturing said preconditioned callus on a third medium which comprises mineral salts consisting of magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA, vitamins consisting of thiamine, pyridoxine, myo-inositol, riboflavin, calcium pantothenate, p-aminobenzoic acid, niacin, choline and folic acid, sucrose and a mixture of indoleacetic acid (IAA) and kinetin in an amount sufficient to ensure shoot formation, and
(d) subculturing said shoot on a fourth medium which comprises mineral salts consisting of magnesium sulfate, calcium chloride, monopotassium phosphate, potassium nitrate, ammonium nitrate, boric acid, manganese sulfate, zinc sulfate, sodium molybdate, copper sulfate, cobalt chloride, potassium iodide, iron sulfate and disodium-EDTA, vitamins consisting of myo-inositol and thiamine, sucrose and IAA in an amount sufficient to ensure root formation, whereby plants are obtained.

18. The process of claim 17 wherein said tissue is immature embryos.

19. The process of claim 17 wherein said callus is subcultured on a maintenance medium which comprises mineral salts consisting of magnesium sulfate, calcium chloride, monosodium phosphate, potassium nitrate, ammonium sulfate, boric acid, manganese sulfate, zinc sulfate, sodium molybdate, copper sulfate, cobalt chloride, potassium iodide and chelated iron, vitamins consisting of nicotinic acid, thiamine, pyridoxine and myo-inositol, amino acids consisting of alanine, glutamine, serine, tryptophan and cysteine, sucrose and ABA in an amount sufficient to ensure callus maintenance prior to subculturing on said second medium.

20. The process of claim 19 wherein the concentrations of ABA, 2,4-D, IAA, BA and kinetin are:
(1) 5.0–12.0 $\mu$M 2,4-D and 1.0–7.0 $\mu$M ABA in said first medium;
(2) 0.05–1.0 $\mu$M ABA in said second medium;
(3) 0.5–2.0 $\mu$M BA or 1.0–4.0 $\mu$M ABA and 0.5–2.0 $\mu$M BA in said second medium;
(4) 0.3–3.0 $\mu$M IAA and 0.5–9.0 $\mu$M kinetin in said third medium, and
(5) 0.05–0.5 $\mu$M IAA in said fourth medium.

21. The process of claim 20 wherein the concentration of sucrose is:
(1) 7%–14% in said first medium;
(2) 7%–14% in said maintenance medium;
(3) 6%–8% in said second medium;
(4) 2%–4% in said third medium, and
(5) 2%–3% in said fourth medium.

22. The process of claim 21 wherein said mineral salts of said first, maintenance and second media are the B5 mineral salts modified so that the concentration of the copper sulfate is 0.0025 mg/l and the concentration of the potassium iodide is 0.075 mg/l and the chelated iron contains 0.81 mg/l iron.

23. The process of claim 21 wherein said vitamins of said first, maintenance and second media are Chandler vitamins.

24. The process of claim 21 wherein said amino acids of said first, maintenance and second media are Chandler amino acids.

25. The process of claim 21 wherein said mineral salts of said third and fourth media are MS mineral salts.

26. The process of claim 21 wherein said vitamins of said third medium are Henderson vitamins, modified to contain 100.5 mg/l myo-inositol and 0.5 mg/l thiamine hydrochloride.

27. The process of claim 21 wherein the concentration is said fourth medium of myo-inositol is 100 mg/l and of thiamine hydrochloride is 0.4 mg/l.

28. A process for regenerating sunflower plants from cell or tissue culture through embryogenesis and organogenesis which comprises the steps of:
(a) culturing tissue obtained from a sunflower plant on a first medium which comprises the B5 mineral salts modified so that the concentration of the copper sulfate is 0.0025 mg/l and the concentration of the potassium iodide is 0.075 mg/l and the chelated iron contains 0.81 mg/l iron, the Chandler vitamins, the Chandler amino acids, 7%–14% sucrose and a mixture of 1.0–7.0 $\mu$M abscisic acid (ABA) and 5.0–12.0 $\mu$M 2,4-dichlorophenoxyacetic acid (2,4-D) to ensure callus formation;
(b) subculturing said callus on a second medium which comprises B5 mineral salts modified so that the concentration of the copper sulfate is 0.0025 mg/l and the concentration of the potassium iodide is 0.075 mg/l and the chelated iron contains 0.81 mg/l iron, the Chandler vitamins, the Chandler amino acids, 4%–8% sucrose and 0.5–2.0 $\mu$M 6-benzylaminopurine (BA) or a mixture of 1.0–4.0 $\mu$M ABA and 0.5–2.0 $\mu$M BA to ensure callus preconditioning;
(c) subculturing said preconditioned callus on a third medium which comprises the MS mineral salts, the Henderson vitamins modified to contain 100.5 mg/l myo-inositol and 0.5 mg/l thiamine hydrochloride, 2%–4% sucrose and a mixture of 0.3–3.0 μM indoleacetic acid (IAA) and 0.5–9.0 μM kinetin, to ensure shoot formation, and (d) subculturing said shoot on a fourth medium which comprises the MS mineral salts, 100 mg/l myo-inositol, 0.4 mg/l thiamine hydrochloride, 2%–3% sucrose, and 0.05–0.5 μM IAA to ensure root formation, whereby plants are obtained.

29. The process of claim 28 wherein said tissue is immature embryos.

30. The process of claim 28 wherein said callus is subcultured on a maintenance medium which comprises B5 mineral salts modified so that the concentration of the copper sulfate is 0.0025 mg/l and the concentration of the potassium iodide is 0.075 mg/l and the chelated iron contains 0.81 mg/l iron, the Chandler vitamins, the Chandler amino acids, 7%–14% sucrose and 0.05–1.0 μM ABA to ensure callus maintenance prior to subculturing on said second medium.

31. The process of claim 30 wherein the concentration of sucrose is:
 (1) 12% in said first medium;
 (2) 12% in said maintenance medium;
 (3) 6% in said second medium;
 (4) 3% in said third medium, and
 (5) 2% in said fourth medium.

32. The process of claim 31 wherein the concentrations of ABA, 2,4-D, BA, IAA and kinetin are:
 (1) 10 μM 2,4-D and 5 μM ABA in said first medium;
 (2) 1 μM ABA in said maintenance medium;
 (3) 1 μM BA or 3 μM ABA and 1 μM BA in said second medium;
 (4) 0.3 μM IAA and 5.0 μM kinetin in said third medium, and
 (5) 0.1 μM IAA in said fourth medium.

* * * * *